(12) United States Patent
Hudson

(10) Patent No.: US 12,042,390 B2
(45) Date of Patent: Jul. 23, 2024

(54) ACETABULAR PROSTHESIS WITH ADJUSTABLE ACETABULAR CUP CAGES

(71) Applicant: DePuy Ireland Unlimited Company, Ringaskiddy (IE)

(72) Inventor: Andrew M. Hudson, Fort Wayne, IN (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 3 days.

(21) Appl. No.: 17/740,813

(22) Filed: May 10, 2022

(65) Prior Publication Data

US 2023/0363918 A1 Nov. 16, 2023

(51) Int. Cl.
*A61F 2/34* (2006.01)
*A61F 2/30* (2006.01)

(52) U.S. Cl.
CPC ...... *A61F 2/34* (2013.01); *A61F 2002/30538* (2013.01); *A61F 2002/30901* (2013.01); *A61F 2002/3412* (2013.01); *A61F 2002/3448* (2013.01); *A61F 2002/3479* (2013.01); *A61F 2002/3487* (2013.01)

(58) Field of Classification Search
CPC .............. A61F 2/34; A61F 2002/30538; A61F 2002/3448; A61F 2002/3479; A61F 2002/3487
See application file for complete search history.

(56) References Cited

U.S. PATENT DOCUMENTS

| | | |
|---|---|---|
| 4,919,675 A | 4/1990 | Dietschi |
| 5,314,490 A | 5/1994 | Wagner et al. |
| 5,425,778 A | 6/1995 | Zichner et al. |
| 5,702,477 A | 12/1997 | Capello et al. |
| 5,871,548 A | 2/1999 | Sanders et al. |
| 5,879,399 A | 3/1999 | Church |
| 5,931,870 A | 8/1999 | Cuckler et al. |
| 6,340,370 B1 | 1/2002 | Willert et al. |
| 6,416,553 B1 | 7/2002 | White et al. |
| 6,454,809 B1 | 9/2002 | Tornier |
| 6,458,161 B1 | 10/2002 | Gibbs et al. |
| 6,908,486 B2 | 6/2005 | Lewallen |

(Continued)

FOREIGN PATENT DOCUMENTS

| | | |
|---|---|---|
| CA | 2586510 | 11/2007 |
| EP | 3033050 | 6/2016 |

(Continued)

OTHER PUBLICATIONS

International Search Report and Written Opinion Completed Jul. 5, 2023 in PCT/EP2023/062292.

*Primary Examiner* — Brian A Dukert
(74) *Attorney, Agent, or Firm* — Barnes & Thornburg LLP

(57) ABSTRACT

An acetabular prosthesis for use in a hip arthroplasty surgical procedure includes an acetabular cup cage assembly including an outer cup cage and an inner cup cage. The outer cup cage includes a hemispherical cup and a mounting flange. Similarly, the inner cup cage also includes a hemispherical cup and a corresponding mounting flange. The hemispherical cup of the inner cup cage is sized to be received into the hemispherical cup of the outer cup cage, and the two cup cages are rotatable relative to each other to position the mounting flanges into a desired position on a hip bone of a patient.

19 Claims, 11 Drawing Sheets

(56) References Cited

U.S. PATENT DOCUMENTS

| | | |
|---|---|---|
| 7,291,177 B2 | 11/2007 | Gibbs |
| 7,682,399 B2* | 3/2010 | Shields .................... A61F 2/34 |
| | | 623/22.32 |
| 7,713,306 B2 | 5/2010 | Gibbs |
| 8,021,432 B2 | 9/2011 | Meridew et al. |
| 8,123,814 B2 | 2/2012 | Meridew et al. |
| 8,123,816 B2 | 2/2012 | Shields et al. |
| 8,597,365 B2 | 12/2013 | Meridew |
| 9,375,316 B2 | 6/2016 | Meridew et al. |
| 11,517,441 B2 | 12/2022 | Lee et al. |
| 2003/0153982 A1 | 8/2003 | Pria |
| 2004/0199258 A1 | 10/2004 | Macara |
| 2005/0288793 A1* | 12/2005 | Dong ....................... A61F 2/34 |
| | | 623/22.32 |
| 2006/0190089 A1 | 8/2006 | Montoya et al. |
| 2012/0083895 A1 | 4/2012 | Conway et al. |
| 2016/0317311 A1 | 11/2016 | Meridew |
| 2022/0151792 A1 | 5/2022 | Lee et al. |
| 2022/0313444 A1 | 10/2022 | Lewis et al. |

FOREIGN PATENT DOCUMENTS

| | | |
|---|---|---|
| FR | 2785522 A1 | 5/2000 |
| WO | 2020198219 A1 | 10/2020 |

\* cited by examiner

ACETABULAR PROSTHESIS WITH ADJUSTABLE ACETABULAR CUP CAGES

TECHNICAL FIELD

The present disclosure relates generally to orthopaedic surgical instruments and, more particularly, to acetabular prosthetic components.

BACKGROUND

Joint arthroplasty is a well-known surgical procedure by which a diseased and/or damaged natural joint is replaced by a prosthetic joint. Typical artificial joints include hip prostheses, knee prostheses, shoulder prostheses, ankle prostheses, and wrist prostheses, among others. In a hip arthroplasty procedure, for example, at least a portion of a patient's hip ball and socket joint is replaced with one or more corresponding prosthetic components. In such procedures, the socket portion of the joint, known as the acetabulum, may be replaced with one or more acetabular prosthetic components (e.g., an acetabular cup or shell that fits within the acetabulum and a liner that fits within the acetabular cup to act as a bearing surface). Similarly, the ball portion of the joint, known as the femoral head, may be replaced with a femoral head prosthetic component.

In some hip arthroplasty procedures, the standard acetabular prosthesis, which includes an acetabular cup and associated cup liner, may be further augmented with additional acetabular prosthetic components. For example, in surgical cases in which a patient has significant bone loss in the area of the acetabulum and/or in some revision procedures, an acetabular cup cage may be used to improve the fixation of the acetabular cup. A typical acetabular cup cage includes a hemispherical cup to receive the acetabular cup and a fixed mounting flange to secure the hemispherical cup to the hip bone of the patient (i.e., the boney anatomy surrounding the acetabulum of the patient's hip). However, due to the fixed orientation of the mounting flange and the variability of the geometry of patient's hip bone, it can be difficult for an orthopaedic surgeon to properly orientate a typical acetabular cup cage to achieve the desired fixation on the patient's boney anatomy.

SUMMARY

According to an aspect of the present disclosure, an acetabular prosthesis for use in a hip arthroplasty surgical procedure includes an outer cup cage and an inner cup cage. The outer cup cage includes a first hemispherical cup and a first mounting flange extending from a rim of the first hemispherical cup. The inner cup cage includes a second hemispherical cup and a second mounting flange extending from a rim of the second hemispherical cup. The second hemispherical cup may be sized to nest within the first hemispherical cup. Additionally, when the second hemispherical cup is nested within the first hemispherical cup, each of the inner cup cage and the outer cup cage are rotatable relative to each other about an axis extending through an apex of each of the first and second hemispherical cups to selectively position the first and second mounting flanges.

In some embodiments, the first mounting flange may be embodied as an ilium mounting flange having a first mounting aperture and configured to be secured to an ilium of a patient's hip via the first mounting aperture. Additionally, in some embodiments, the second mounting flange may be embodied as an ischium mounting flange having a second mounting aperture and configured to be secured to an ischium of the patient's hip via the second mounting aperture. Furthermore, in some embodiments, the first mounting flange may have a surface area that is larger than a surface area of the second mounting flange. The first and second mounting flanges may also be malleable to allow morphing of the shape of the first and second mounting flanges.

Additionally, in some embodiments, at least one of the first and second hemispherical cup is semi-hemispherical. In some embodiments, the first hemispherical cup has a diameter that is greater than a diameter of the second hemispherical cup. Additionally, in some embodiments, each of the first and second hemispherical cups include a plurality of mounting holes defined therethrough. In such embodiments, each of the inner cup cage and the outer cup cage may be rotatable to align at least one mounting hole of the first hemispherical cup with at least one mounting hole of the second hemispherical cup.

In some embodiments, the first hemispherical cup may include an inner concave surface and an outer convex surface. In such embodiments, the rim of the first hemispherical cup extends from the inner concave surface to the outer convex surface of the first hemispherical cup. Additionally, in some embodiments, the second hemispherical cup includes an inner concave surface and outer convex surface. In such embodiments, the rim of the second hemispherical cup extends from the inner concave surface to the outer convex surface of the second hemispherical cup.

Additionally, in some embodiments, the first hemispherical cup of the outer cup cage may include an elongated track, and the second hemispherical cup may include a guide tab received in the elongated track. When the inner cup cage and the outer cup cage are rotated about the axis, the guide tab of the second hemispherical cup moves within the elongated track of the first hemispherical cup. In some embodiments, the elongated track may include an elongated opening, and the guide tab of the second hemispherical cup may be insertable into the elongated opening when the second hemispherical cup is nested into the first hemispherical cup. Additionally, in some embodiments, the guide tab may be captured within elongated track such that the inner cup cage is secured to the outer cup cage.

According to another aspect of the disclosure, a method of performing an orthopaedic surgical procedure on a hip of a patient includes inserting an outer cup cage of an acetabular prosthesis into an acetabulum of the patient and inserting an inner cup cage of the acetabular prosthesis into the outer cup cage. The outer cup cage may include a first hemispherical cup and a first mounting flange extending from a rim of the first hemispherical cup. Similarly, the inner cup cage may include a second hemispherical cup and a second mounting flange extending from a rim of the second hemispherical cup. In some embodiments, inserting the inner cup cage may include nesting the second hemispherical cup into the first hemispherical cup. The method may also include rotating at least one of the inner cup cage and the outer cup cage relative to each other about an axis extending through an apex of each of the first and second hemispherical cups while the second hemispherical cup is nested within the first hemispherical cup to position the first mounting flange and the second mounting flange in corresponding desired positions and securing the first mounting flange and the second mounting flange to the hip bone of the patient.

In some embodiments, the method may also include securing the first and second hemispherical cups to the acetabulum of the patient. Additionally, in some embodiments, the method may include inserting an acetabular cup prosthesis into the second hemispherical cup of the inner cup cage. In such embodiments, the method may further include securing the first and second hemispherical cups and the acetabular cup prosthesis to the acetabulum of the patient using bone cement.

In some embodiments, inserting the inner cup cage into outer cup cage may include inserting a guide tab of the second hemispherical cup of the inner cup cage into an elongated track of the first hemispherical cup of the outer cup cage. In such embodiments, rotating the at least one of the inner cup cage and the outer cup cage relative to each other may include moving the guide tab within the elongated track.

Additionally, in some embodiments, the first mounting flange may be embodied as an ilium mounting flange, and the second mounting flange may be embodied as an ischium mounting flange. In such embodiments, rotating the at least one of the inner cup cage and the outer cup cage relative to each other may include positioning the ilium mounting flange onto the ilium of the hip of the patient and positioning the ischium mounting flange onto the ischium of the hip of the patient.

According to further aspect of the present disclosure, an acetabular prosthesis for use in a hip arthroplasty surgical procedure includes an outer cup cage, an inner cup cage, and an acetabular cup prosthesis. The outer cup cage includes a first semi-hemispherical cup and an ilium mounting flange extending from a rim of the first semi-hemispherical cup. The inner cup cage includes a second semi-hemispherical cup and an ischium extending from a rim of the second semi-hemispherical cup. Additionally, the second semi-hemispherical cup has an outer diameter smaller than an inner diameter of the first semi-hemispherical cup that allows the second semi-hemispherical cup to be received within the first hemispherical cup.

The acetabular cup prosthesis includes an outer diameter that is smaller than an inner diameter of the second semi-hemispherical cup that allows the acetabular cup prosthesis to be received within the second semi-hemispherical cup. Additionally, when the second semi-hemispherical cup is received within the first semi-hemispherical cup, each of the inner cup cage and the outer cup cage are rotatable relative to each other to independently position the ilium flange and the ischium flange.

In some embodiments, the first semi-hemispherical cup of the outer cup cage includes an elongated track and the second semi-hemispherical cup includes a guide tab that is receivable in the elongated track. In such embodiments, when the inner cup cage and the outer cup cage are rotated about the axis, the guide tab of the second semi-hemispherical cup moves within the elongated track of the first semi-hemispherical cup.

BRIEF DESCRIPTION OF THE DRAWINGS

The detailed description particularly refers to the following figures, in which.

DETAILED DESCRIPTION OF THE DRAWINGS

Figure 1:
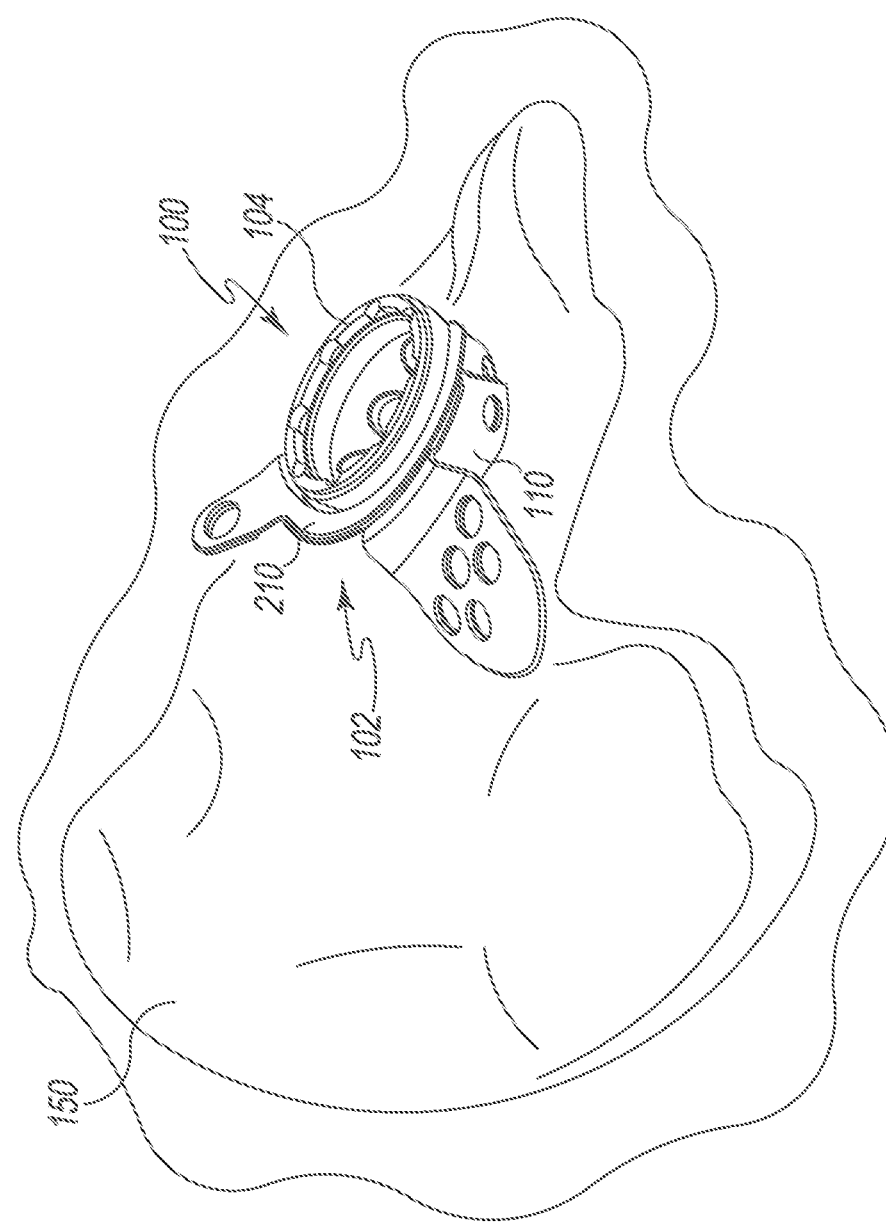
FIG. 1 is a perspective view of an acetabular prosthesis including an acetabular cup cage assembly and an acetabular cup implanted into a hip of a patient.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring to FIG. 1, an illustrative acetabular prosthesis 100 includes an acetabular cup cage assembly 102 and an acetabular cup 104, each of which is configured for implantation into an acetabulum of a hip bone 150 of a patient during the performance of a corresponding orthopaedic surgical procedure. As discussed in more detail below, the acetabular cup cage assembly 102 provides additional support and fixation to the patient's hip bone for the acetabular cup 104 and may be used in various situations, including those cases in which the patient's hip bone 150 has significant bone loss or deterioration. Additionally, as discussed in more detail below, the acetabular cup cage assembly 102 is adjustable to modify the mounting locations of the acetabular cup cage assembly 102 to thereby compensate for the particular geometry and/or bone loss of the patient's hip bone (e.g., the geometry of the patient's acetabulum, ilium, and ischium).

Figure 2:
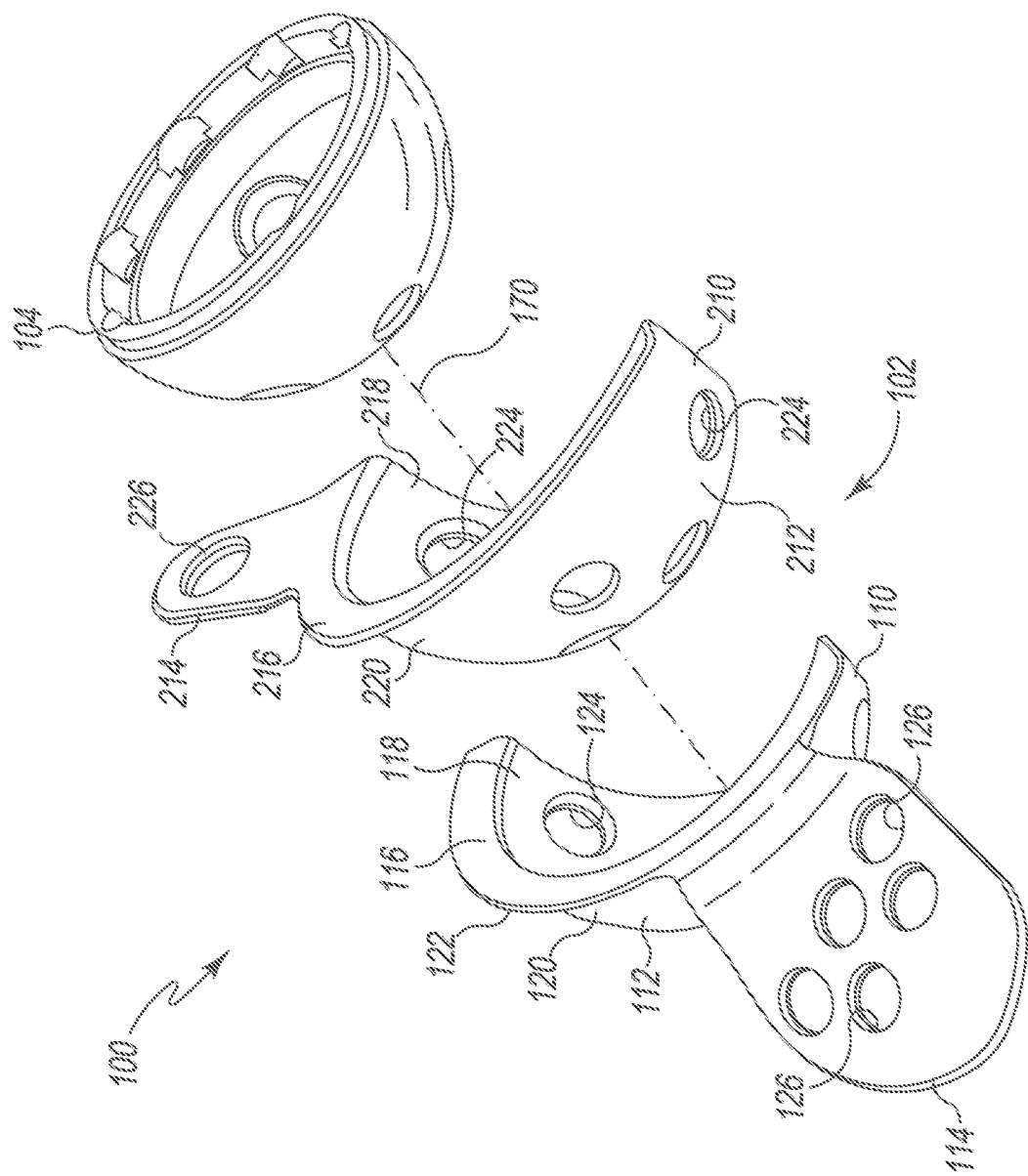
FIG. 2 is an exploded, perspective view of an embodiment of the acetabular prosthesis of FIG. 1.

As shown in FIG. 2, the illustrative acetabular cup cage assembly 102 of the acetabular prosthesis 100 includes an outer cup cage 110 and an inner cup cage 210, which are separate from each other and are independently movable as discussed in more detail below. Additionally, as discussed further below, the inner cup cage 210 is configured to be nested or otherwise received in the outer cup cage 110. Similarly, the acetabular cup 104 is configured to be received in the inner cup cage 210. The acetabular cup 104, the inner cup cage 210, and the outer cup cage 110 may secured to the patient's acetabulum, and the inner and outer cup cages 110, 210 may also be secured to the surrounding bony area, such as the patient's ilium and ischium as discussed below.

The outer cup cage 110 includes a hemispherical cup 112 and a mounting flange 114, which extends from a rim 116 of the hemispherical cup 112. Similarly, the inner cup cage 210 includes a hemispherical cup 212 and a mounting flange 214 that extends from a rim 216 of the hemispherical cup 212. As discussed below, the hemispherical cup 212 of the inner cup cage 210 is shaped and sized to be received into the hemispherical cup 112 of the outer cup cage 110 such that the inner cup cage 210 can be nested into the outer cup cage 110 as shown in FIG. 1. It should be appreciated that, as used herein, the term "hemispherical" is intended to be a broad term that includes hemispherical, semi-hemispherical, and other geometry that is similar to a hemisphere but not necessarily defining a perfect hemisphere. For example, the illustrative hemispherical cups 112, 212 are semi-hemispherical as shown in FIG. 2 and approximate a quarter of sphere. However, in other embodiments, the hemispherical cups 112, 212 may have a full hemispherical shape or a shape between semi-hemispherical and full hemispherical.

Figure 3:
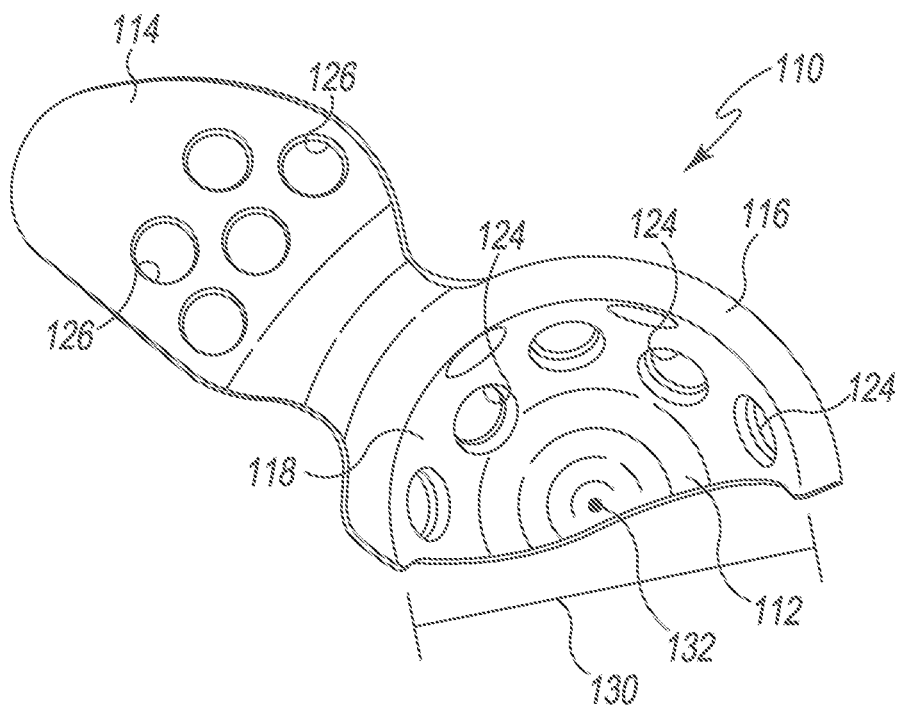
FIG. 3 is a top plan view of an outer cup cage of the acetabular cup cage assembly of FIG. 2.

As shown best in FIGS. 2 and 3, the hemispherical cup 112 of the outer cup cage 110 includes an inner, concave surface 118 and an outer, convex surface 120 opposite the inner surface 118. The rim 116 extends from the inner surface 118 to the outer surface 120 and further extends radially outward from the outer surface 120 to form a lip of 122 of the hemispherical cup 112. The rim 116 provides support for the rim 216 of the inner hemispherical cup 212 and may also contact the rim of the patient's acetabulum in some implementations. In some embodiments, the outer surface 120 of the hemispherical cup 112 may have an increased surface roughness and/or a porous coating to improve fixation of the hemispherical cup 112 to the patient's acetabulum. Additionally, the hemispherical cup 112 includes one or more mounting apertures 124 that extend completely through the hemispherical cup 112 (i.e., from the inner surface 118 to the outer surface 120). In use, as discussed below, the mounting aperture(s) 124 may be used to secure the hemispherical cup 112 to the patient's acetabulum using associated securing devices (e.g., bone screws), bone cement, and/or other securing mechanisms.

As discussed above, the flange 114 extends from the rim 116 of the hemispherical cup 112. The flange 114 is configured for attachment to the ilium of the patient's hip bone 150 (or other portion of the patent's hip bone 150) and is illustratively larger than the flange 214 of the hemispherical cup 212 of the inner cup cage 210 (i.e., the illustrative flange 114 has a larger surface area than the flange 214). However, in other embodiments, the flange 114 and the flange 214 may be similarly sized and/or shaped.

To facilitate attachment of the flange 114 to the patient's ilium, the flange 114 includes one or more mounting apertures 126, which extend completely through the flange 114. Illustratively, the flange 114 includes multiple apertures 126, but may only include a single mounting aperture in other embodiments. As discussed in more detail below, the mounting apertures 126 may be used to secure the flange 114 to the patient's ilium (or other area of the patient's hip bone 150) using a suitable securing device such as a bone screw.

Figure 4:
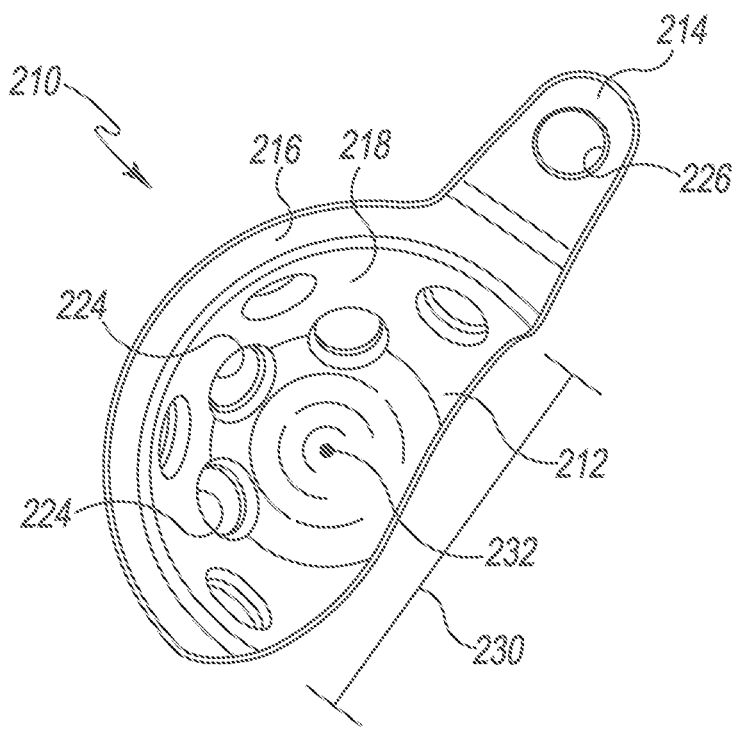
FIG. 4 is a top plan view of an inner cup cage of the acetabular cup cage assembly of FIG. 2.

As shown best in FIGS. 2 and 4, the hemispherical cup 212 of the inner cup cage 210 is similar to the hemispherical cup 112 of the outer cup cage 110. For example, the hemispherical cup 212 also includes an inner, concave surface 218 and an outer, convex surface 220 opposite the inner surface 118. The rim 216 extends from the inner surface 218 to the outer surface 220 and further extends radially outward from the outer surface 220 to form a lip of 222 of the hemispherical cup 212. When the hemispherical cup 212 is nested into the hemispherical cup 112 of the outer cup cage 110, the rim 216 of the hemispherical cup 212 may be configured to contact and be supported by the rim 116 of the hemispherical cup 112.

In some embodiments, the outer surface 220 of the hemispherical cup 212 of the inner cup cage 210 and/or the inner surface 118 of the hemispherical cup 112 of the outer cup cage 110 may have an increased surface roughness and/or a porous coating such that the outer surface 220 and the inner surface 118 cooperate to provide an amount of resistance to relative movement between the hemispherical cups 112, 212. In this way and as discussed in more detail below, an orthopaedic surgeon may rotate the hemispherical cups 112, 212 to a desired position and that desired position is at least somewhat maintained by the "locking" nature of the outer surface 220 and the inner surface 118. However, in other embodiments, the outer surface 220 of the hemispherical cup 212 and the inner surface 118 of the hemispherical cup 212 may be relatively smooth, promoting relative movement between the hemispherical cups 112, 212.

Similar to the hemispherical cup 112 of the outer cup cage 110, the hemispherical cup 212 of the inner cup cage 210 includes one or more mounting apertures 224 that extend completely through the hemispherical cup 212 (i.e., from the inner surface 218 to the outer surface 220). In use, the mounting aperture(s) 224 may be used to secure the hemispherical cup 212 to the patient's acetabulum using associated securing devices (e.g., bone screws), bone cement, and/or other securing mechanisms. To do so, as discussed in more detail below, the orthopaedic surgeon may align, completely or partially, one more of the mounting apertures 224 of the hemispherical cup 212 of the inner cup cage 210 with a corresponding mounting aperture 124 of the hemispherical cup 112 of the outer cup cage 110.

As discussed above, the flange 214 extends from the rim 216 of the hemispherical cup 212. The flange 214 is configured for attachment to the ischium of the patient's hip bone 150 and is illustratively smaller than the flange 114 of the hemispherical cup 112 of the outer cup cage 110 (i.e., the illustrative flange 214 has a smaller surface area than the flange 114). To facilitate attachment of the flange 214 to the patient's ischium, the flange 214 includes a mounting apertures 226, which extends completely through the flange 214. Although the illustrative flange 214 includes a single mounting aperture 226, the flange 214 may include additional mounting apertures 226 in other embodiments. As discussed in more detail below, the mounting apertures 226 may be used to secure the flange 214 to the patient's ischium (or other area of the patient's hip bone 150) using a suitable securing device such as a bone screw.

The outer cup cage 110 and the inner cup cage 210 may be formed from any material capable of providing support and fixation for the acetabular cup 104. Illustratively, the cup cages 110, 210 are formed from a surgical metal material or alloy, such as a titanium alloy. Illustratively, the cup cages 110, 210 are formed from a material and/or have a thickness that allows the flanges 114, 214 to be hand-malleable such that an orthopaedic surgeon can morph the shape of the flanges 114, 214 to accommodate the natural geometry of the patient's hip bone. In other embodiments, however, the cup cages 110, 210 may be made from a more rigid material. Additionally, in some embodiments, the outer cup cage 110 and the inner cup cage 210 may be fabricated via a three-dimensional printing process.

Figure 5:
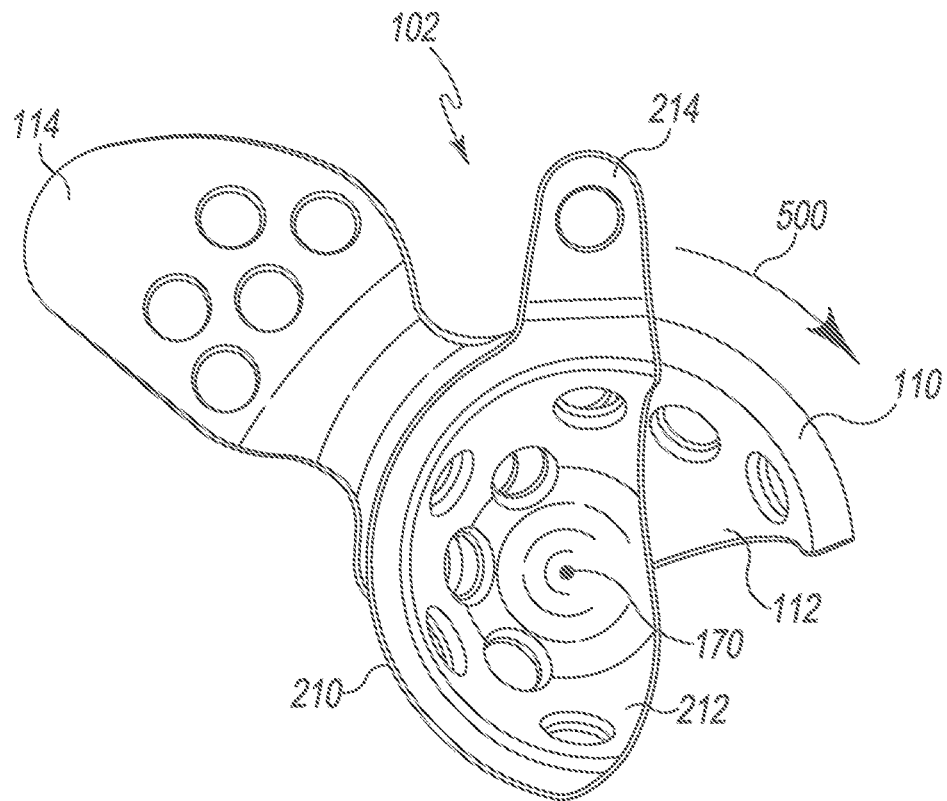
FIG. 5 is a top plan view of the acetabular cup cage assembly of FIG. 1 showing the inner cup cage received within the outer cup cage with a flange of the inner cup cage located at an initial position.
Figure 6:
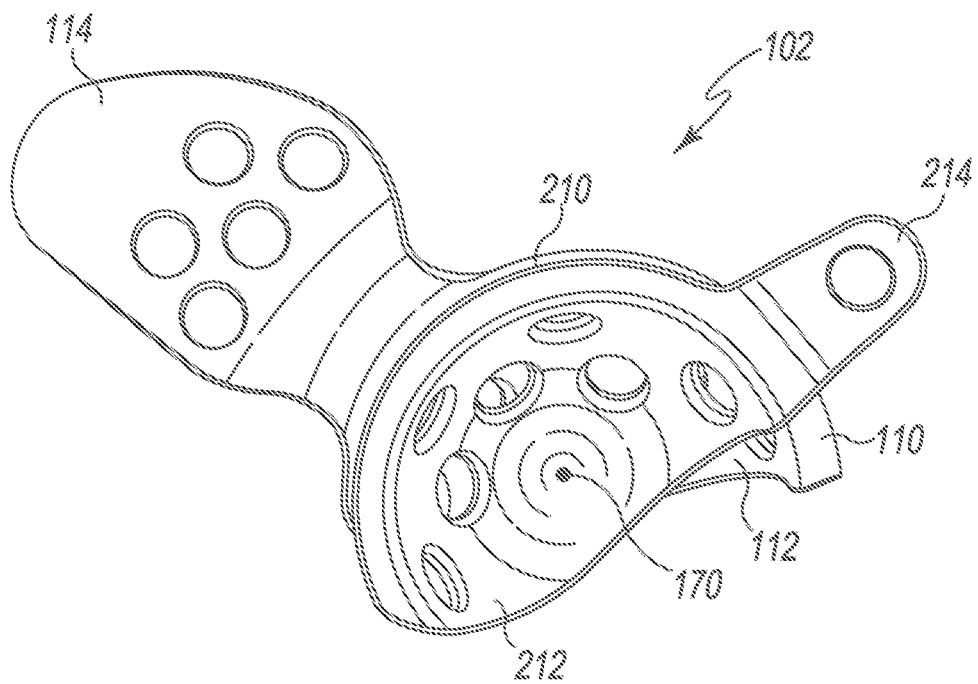
FIG. 6 is a top plan view of the acetabular cup cage assembly of FIG. 5 showing the inner cup cage rotated relative to the outer cup cage with the flange of the inner cup cage located at a new position.

Referring now to FIGS. 5 and 6, as discussed above, the hemispherical cup 212 of the inner cup cage 210 is shaped, sized, and configured to be nested into the hemispherical cup 112 of the outer cup cage 210. That is, the hemispherical cup 212 has an outer diameter 230 (i.e., a diameter distance measured between the outer surface 220 of the hemispherical cup 212) that is slightly smaller than an inner diameter 130 of the hemispherical cup 112 (i.e., a diameter distance measured between the inner surface 118 of the hemispherical cup 112), which allows the hemispherical cup 212 to be received into the hemispherical cup 112.

As discussed above, the outer cup cage 110 and the inner cup cage 210 are separate components in the illustrative embodiment, which allows relative movement between the cup cages 110, 210. That is, as shown in FIG. 5, when hemispherical cup 212 of the inner cup cage 210 is nested or otherwise received in the hemispherical cup 112 of the outer cup cage 110 as shown in FIG. 5, the two cup cages 110, 210 may be rotated relative to each other about an axis 170 (see FIG. 2) that extends through an apex 132 of the hemispherical cup 112 (see FIG. 3) and an apex 232 of the hemispherical cup 212 (see FIG. 4). As such, an orthopaedic surgeon may selectively position the flanges 114, 214 to accommodate for the specific geometry of the patient's hip bone. For example, as shown comparatively between FIGS. 5 and 6, an orthopaedic surgeon may selectively rotate the inner cup cage 110 and/or the outer cup cage 210 about the axis 170 and relative to each other to achieve a desired positioning as indicated by arrow 500. In this way, the orthopaedic surgeon may properly or better position the flange 114 of the outer cup cage 110 on the patient's ilium and properly position the flange 214 of the inner cup cage 210 on the patient's ischium.

Figure 7:
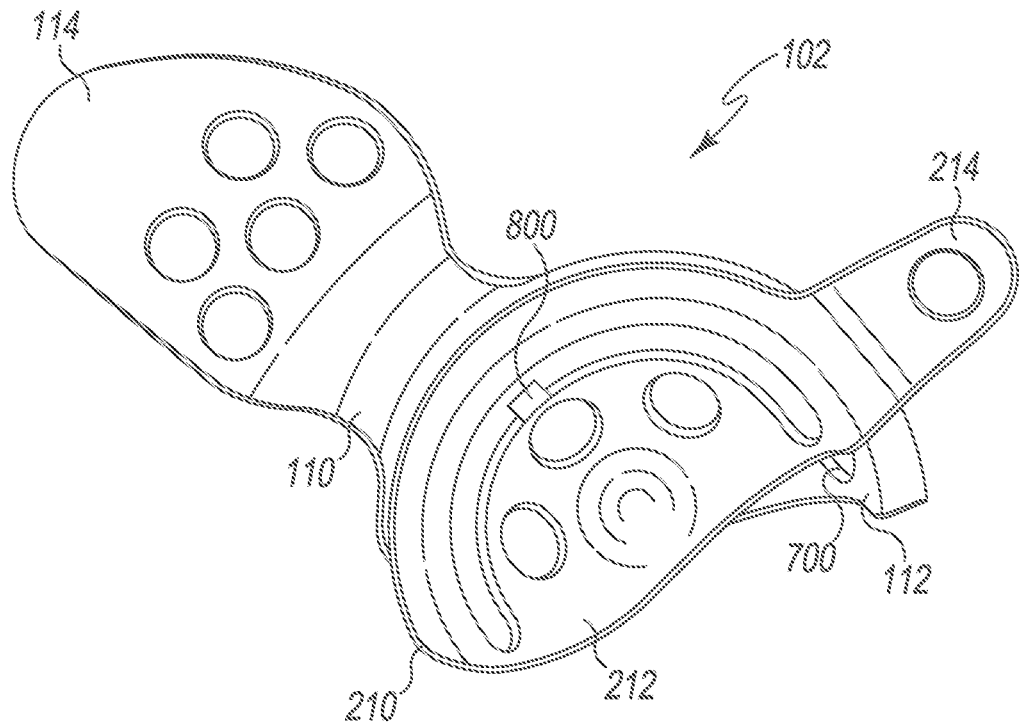
FIG. 7 is a top plan view of another embodiment of the acetabular cup cage assembly of the acetabular prosthesis of FIG. 1 in which the outer cup cage includes an elongated track and the inner cup cage includes a guide tab received in the elongated track of the outer cup cage.
Figure 8:
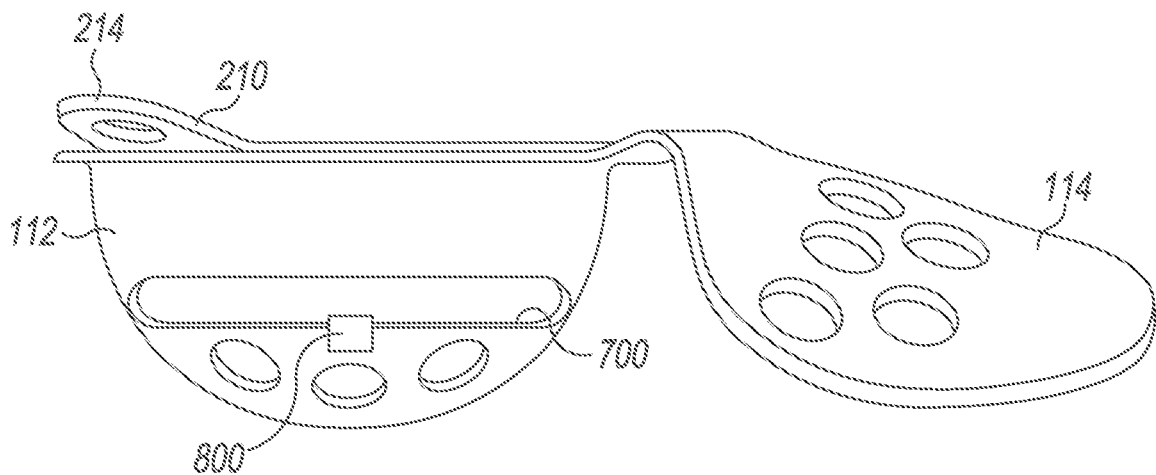
FIG. 8 is a side elevation view of the acetabular cup cage assembly of FIG. 7.

In some embodiments, the outer cup cage 110 and the inner cup cage 210 may be coupled or otherwise attached together, while still facilitating the relative rotation or movement of the cup cages 110, 210. For example, as shown in FIGS. 7 and 8, outer cup cage 110 may include an elongated track or opening 700 and the inner cup cage 210 may include a guide tab 800 in some embodiments. The illustrative elongated track 700 is embodied as a closed track that is defined completely through the hemispherical cup 112, extending from the inner surface 118 to the outer surface 120. The elongated track 700 also extends along an arc of the circumference of the hemispherical cup 112, which allows the cup cages 110, 210 to be rotated about the axis 170. The guide tab 800 of the inner cup cage 210 is received in the elongated track 700 and moves within the elongated track 700 when the cup cages 110, 210 are rotated relative to each other.

In some embodiments, the inner cup cage 210 may also include an elongated track or opening 802 that extends though the hemispherical cup 212 and along an arc of the circumference of the hemispherical cup 212. In such embodiments, the elongated tracks 700, 802 may be partially congruent with each other when the hemispherical cup 212 is received in the hemispherical cup 112, which allows the elongated tracks 700, 802 to be used as a mounting aperture for securing the hemispherical cups 112, 212 to the patient's acetabulum (e.g., via a bone screw or bone cement).

In the illustrative embodiment, the guide tab 800 of the inner cup cage 210 is configured to be inserted into or otherwise received in the elongated track 700 when the inner cup cage 210 is nested into the outer cup cage 110. Similarly, the guide tab 800 may be removed from the elongated track 700 when the inner cup cage 210 is removed from the outer cup cage 110. Alternatively, in other embodiments, the guide tab 800 is captured in the elongated track 700 such that the inner cup cage 210 and the outer cup cage 110 are attached or secured to each other. In such embodiments, the inner cup cage and the outer cup cage 210 may or may not be separable from each other.

Figure 9:
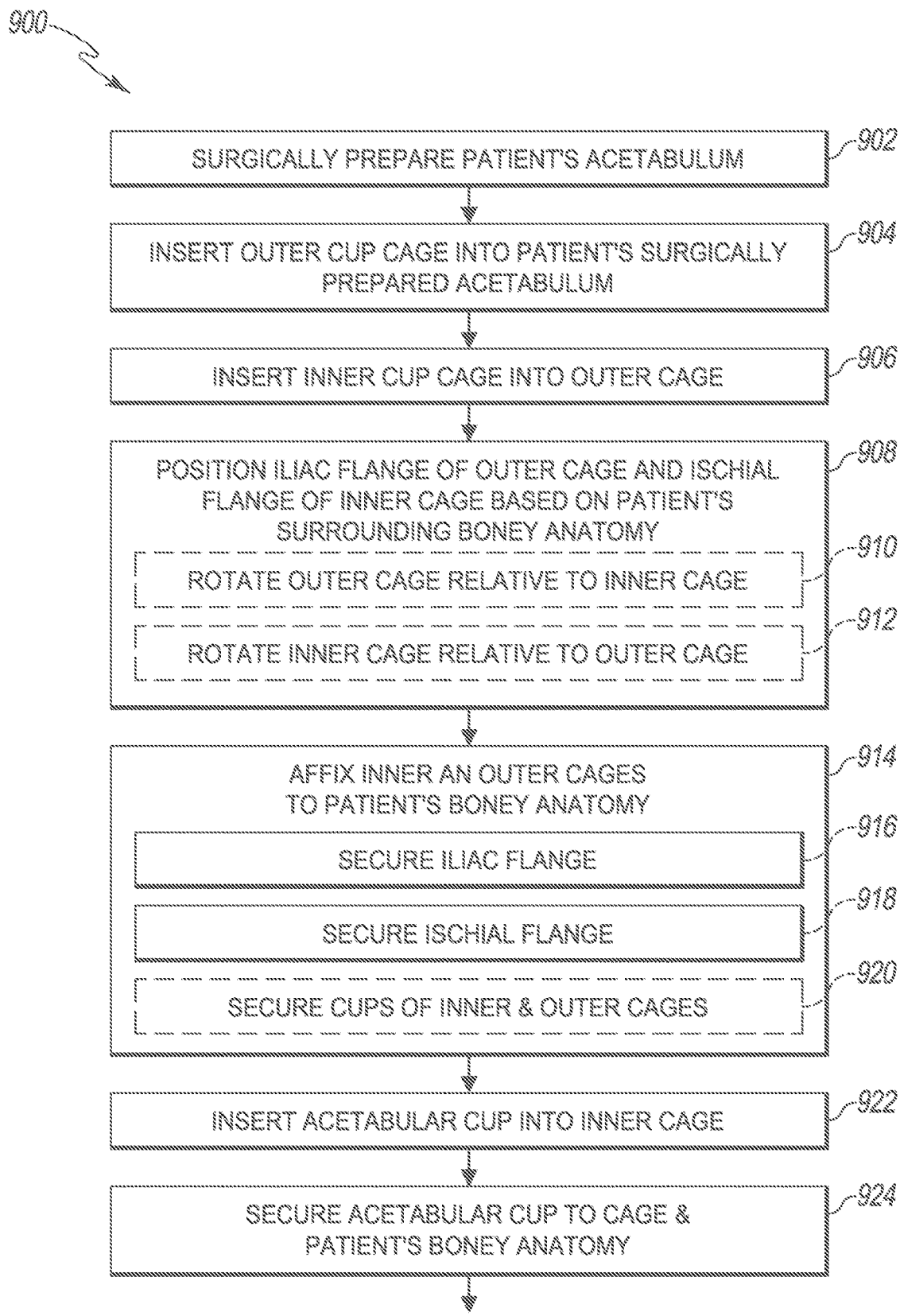
FIG. 9 is a simplified flow diagram of a method for implanting the acetabular prosthesis of FIG. 1.
Figure 10:
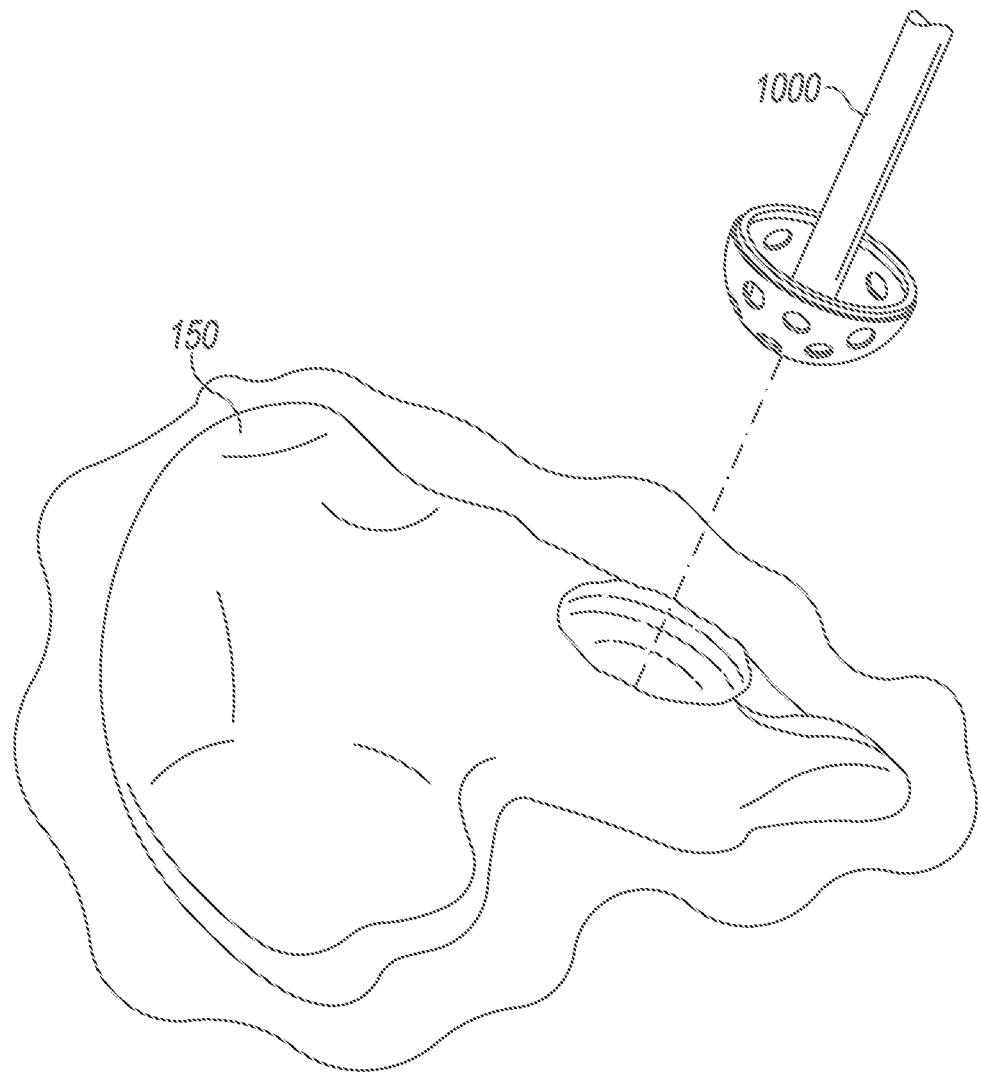
FIG. 10 is a simplified illustration of a hip bone of a patient during an acetabulum reaming procedure of the method of FIG. 9.

Referring now to FIG. 9, in use, an orthopaedic surgeon may perform a method 900 for implanting the acetabular prosthesis 100 into the hip bone 150 of a patient. The method 900 begins with block 902 in which the patient's acetabulum is surgically prepared to receive the acetabular prosthesis 100. For example, as shown in FIG. 10, an orthopaedic surgeon may use a reamer 1000 to ream the patient's acetabulum to prepare the acetabulum to receive the acetabular prosthesis 100.

Figure 11:
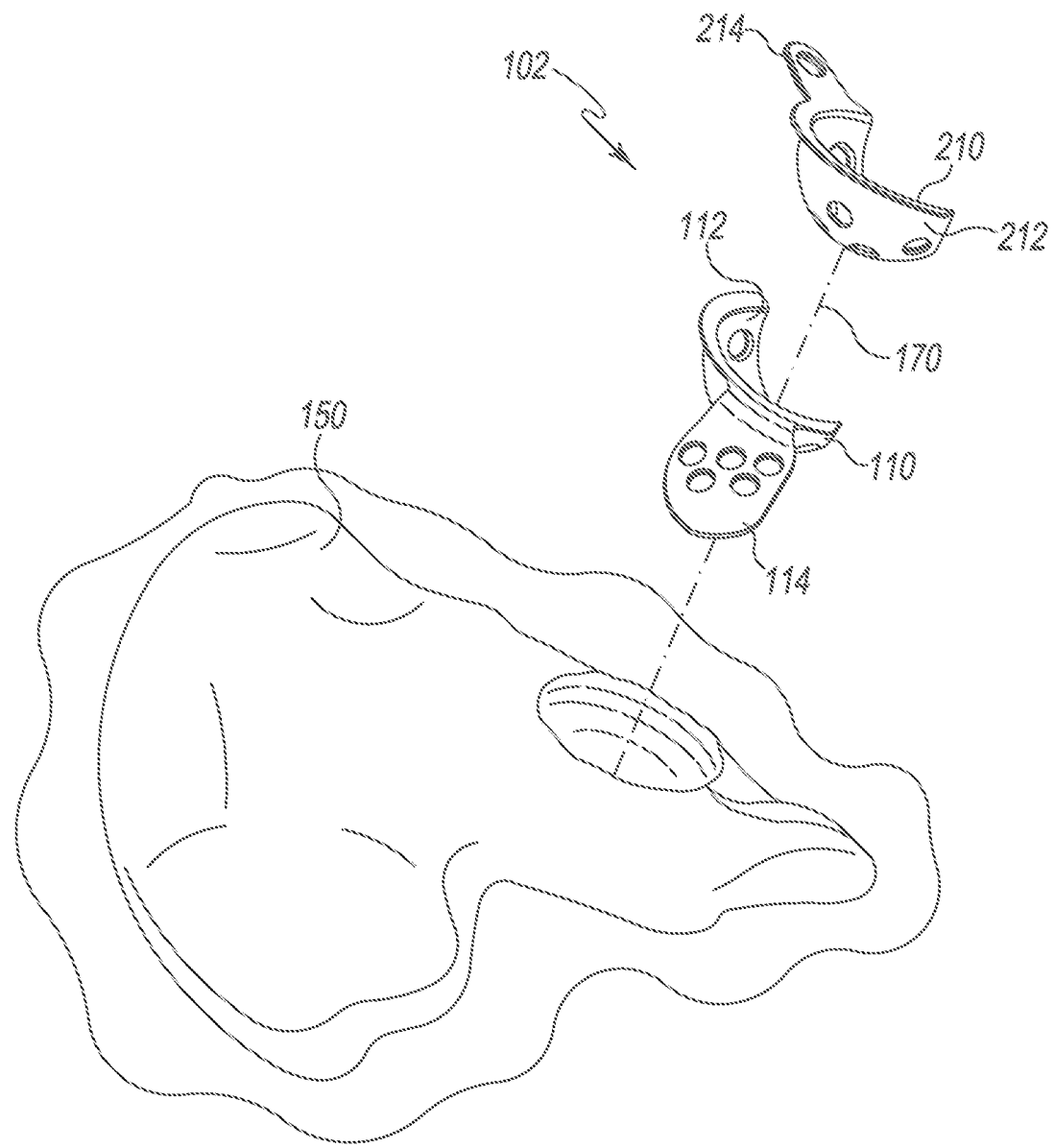
FIG. 11 is a perspective view of the acetabular prosthesis of FIG. 1 being implanted into the hip bone of the patient during the performance of the method of FIG. 9.

After the patient's hip bone 150 has been prepared in block 902, the method 900 advances to block 904. In block 904, the orthopaedic surgeon inserts the outer cup cage 110 into the patient's surgically-prepared acetabulum. Additionally, in block 906, the orthopedic surgeon nests the inner cup cage 210 into the outer cup cage 110. To do so, as shown in FIG. 11, the orthopaedic surgeon inserts the hemispherical cup 212 of the inner cup cage 210 into the hemispherical cup 112 of the outer cup cage 110.

Figure 12:
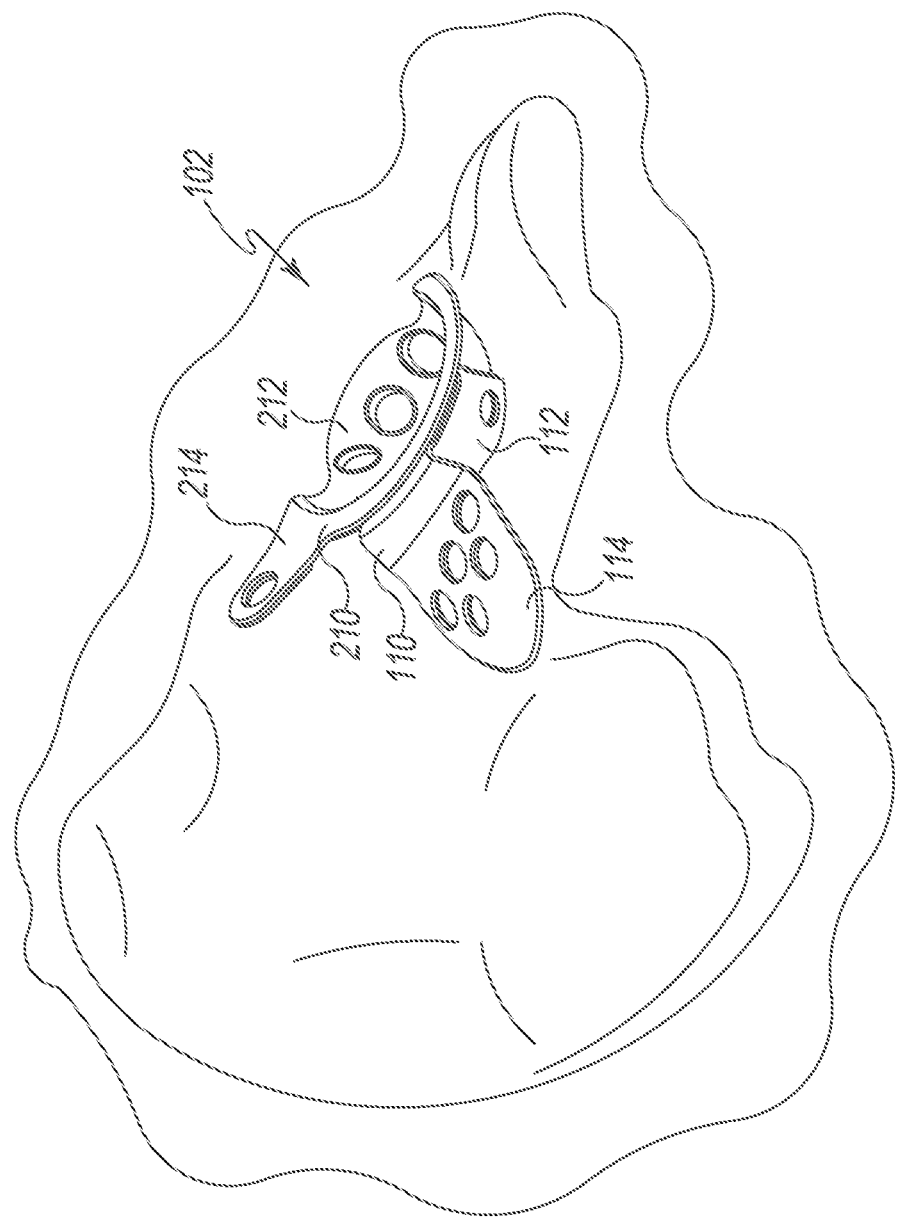
FIG. 12 is a perspective view of the acetabular prosthesis of FIG. 1 implanted into the hip bone of the patient with the inner cup cage rotated to an initial position during the performance of the method of FIG. 9.
Figure 13:
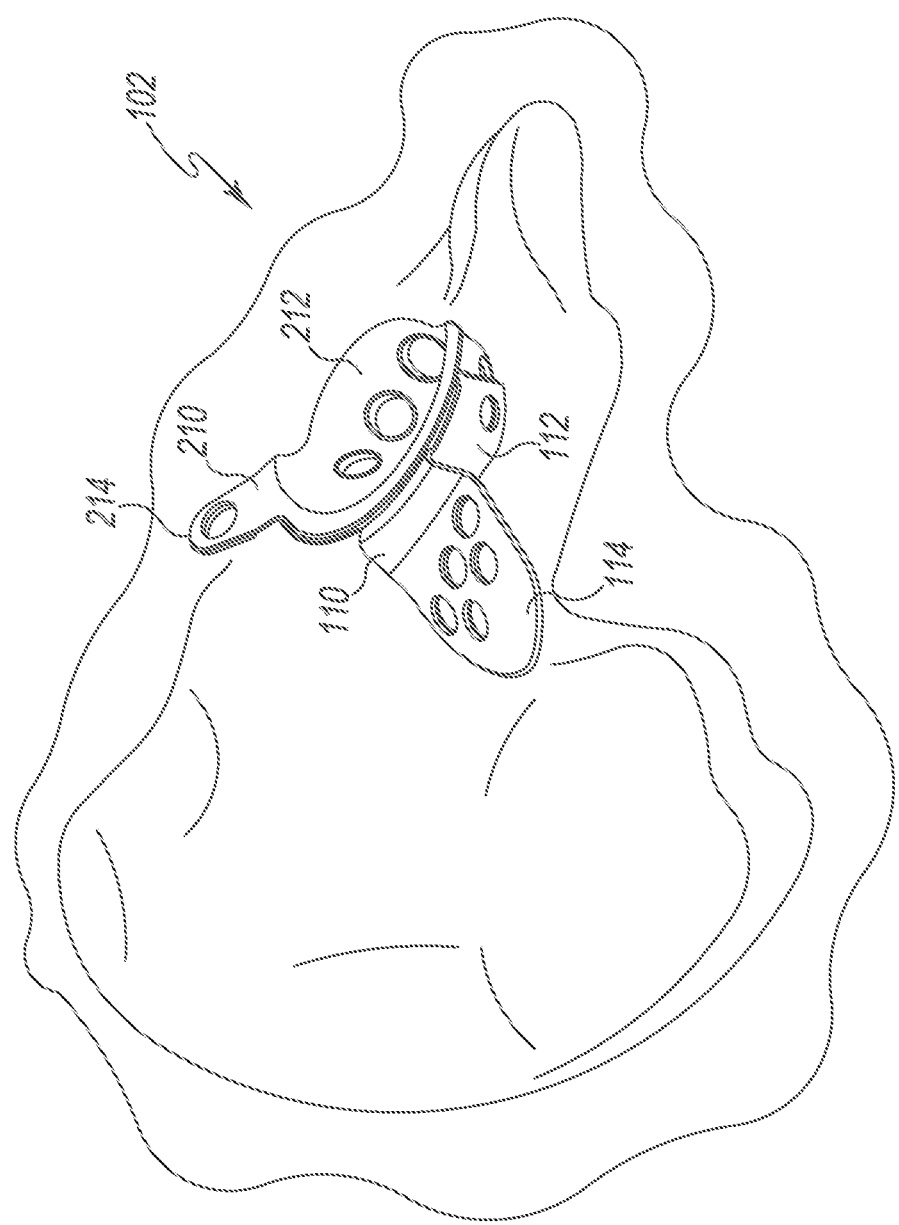
FIG. 13 is a perspective view of the acetabular prosthesis of FIG. 12 having the inner cup cage rotated to a new position to thereby relocate the flange of the inner cup cage to a desired position on the hip bone of the patient during the performance of the method of FIG. 9.

In block 908, the orthopaedic surgeon positions the mounting flange 114 of the outer cup cage 110 and the mounting flange 214 of the inner cup cage 210. To do so, as shown in blocks 910 and 912, the orthopaedic surgeon may rotate the outer cup cage 110 relative to the inner cup cage 210 and/or rotate the inner cup cage 210 relative to the outer cup cage 110 about the axis 170 (see FIG. 11). For example, as shown comparatively between FIGS. 12 and 13, the orthopaedic surgeon may selectively rotate the cup cages 110, 210 to selectively position the mounting flange 114 of the outer cup cage 110 on the patient's ilium and selectively position the mounting flange 214 of the inner cup cage 210 on the patient's ischium.

After the mounting flanges 114, 214 have been properly positioned in block 908, the cup cages 110, 210 may be secured to the patient's hip bone in block 914. To do so, in block 916, the mounting flange 114 of the outer cup cage 110 may be secured to the patient's ilium (or other portion of the patient's hip bone 150) using the mounting apertures 126 and a suitable securing device, such as a bone screw. In some embodiments, multiple apertures 126 and associated securing devices may be used to affix the mounting flange 114. Similarly, in block 918, the mounting flange 214 of the inner cup cage 210 may be secured to the patient's ischium (or other portion of the patient's hip bone 150) using the mounting aperture 126 and a suitable securing device (e.g., a bone screw). Additionally, in some embodiments in block 920, the hemispherical cups 112, 212 of the cup cages 110, 210 may be secured to the patient's acetabulum. For example, the hemispherical cups 112, 212 may be secured via one or more combinations of the mounting apertures 124, 224 and an associated securing device, such as a bone screw. It should be appreciated that not every mounting apertures 124 of the hemispherical cup 112 may be aligned with a corresponding mounting aperture 224 of the hemispherical cup 212 at a particular relative orientation of the hemispherical cups 112, 212. In other embodiments, as discussed below, the hemispherical cups 112, 212 may be secured to the patient's acetabulum using bone cement. In such embodiments, the mounting apertures 124, 224 may act as a conduit to funnel the bone cement onto the hemispherical cups 112, 212 and, subsequently, the acetabular cup 104 to secure all three components of the acetabular prosthesis 100 into the patient's acetabulum.

Figure 14:
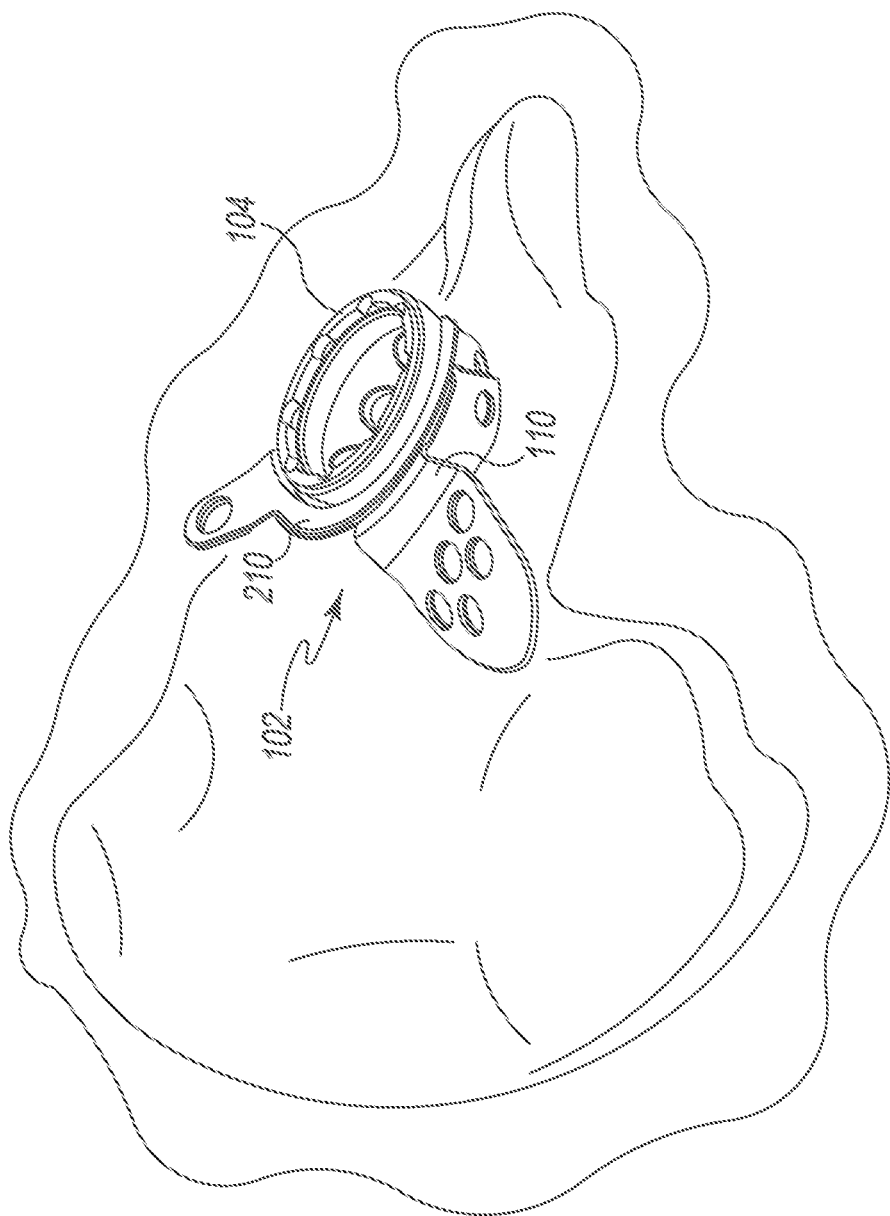
FIG. 14 is a perspective view of the acetabular prosthesis of FIG. 1 implanted into the hip bone of the patient with a femoral component being inserted into the acetabular cup of the acetabular prosthesis during the performance of the method of FIG. 9.

After the inner and outer cup cages 110, 210 have been secured to the patient's hip bone in block 914, the method 900 advances to block 922 in which the acetabular cup 104 is inserted into the hemispherical cup 212 of the inner cup cage 210 as shown in FIG. 14. In block 924, the acetabular cup 104 is secured to the inner cup cage 210 and the patient's acetabulum. For example, as discussed above, the acetabular cup 104 may be secured using bone cement, which secures each of the hemispherical cups 112, 212 and the acetabular cup 104 to the patient's acetabulum.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An acetabular prosthesis for use in a hip arthroplasty surgical procedure, the acetabular prosthesis comprising:
   an outer cup cage having a first semi-hemispherical cup and a first mounting flange extending from a rim of the first semi-hemispherical cup; and
   an inner cup cage having a second semi-hemispherical cup and a second mounting flange extending from a rim of the second semi-hemispherical cup, wherein the second semi-hemispherical cup is sized to nest within the first hemispherical cup,
   wherein, when the second semi-hemispherical cup is nested within the first semi-hemispherical cup, each of the inner cup cage and the outer cup cage are rotatable relative to each other about an axis extending through an apex of each of the first and second semi-hemispherical cups to selectively position the first and second mounting flanges.

2. The acetabular prosthesis of claim 1, wherein the first mounting flange comprises an ilium mounting flange having a first mounting aperture and configured to be secured to an ilium of a patient's hip via the first mounting aperture, and
   wherein the second mounting flange comprises an ischium mounting flange having a second mounting aperture and configured to be secured to an ischium of the patient's hip via the second mounting aperture.

3. The acetabular prosthesis of claim 1, wherein the first mounting flange has a surface area that is larger than a surface area of the second mounting flange.

4. The acetabular prosthesis of claim 1, wherein the first and second mounting flanges are malleable to allow morphing of the shape of the first and second mounting flanges.

5. The acetabular prosthesis of claim 1, wherein the first semi-hemispherical cup has a diameter that is greater than a diameter of the second semi-hemispherical cup.

6. The acetabular prosthesis of claim 1, wherein each of the first and second semi-hemispherical cups include a plurality of mounting holes defined therethrough and wherein each of the inner cup cage and the outer cup cage are rotatable to align at least one mounting hole of the first semi-hemispherical cup with at least one mounting hole of the second semi-hemispherical cup.

7. The acetabular prosthesis of claim 1, wherein the first semi-hemispherical cup comprises an inner concave surface and an outer convex surface and wherein the rim of the first semi-hemispherical cup extends from the inner concave surface to the outer convex surface of the first semi-hemispherical cup, and
   wherein the second semi-hemispherical cup comprises an inner concave surface and outer convex surface and wherein the rim of the second semi-hemispherical cup extends from the inner concave surface to the outer convex surface of the second semi-hemispherical cup.

8. The acetabular prosthesis of claim 1, wherein the first semi-hemispherical cup of the outer cup cage comprises an elongated track and the second semi-hemispherical cup includes a guide tab received in the elongated track,
   wherein, when the inner cup cage and the outer cup cage are rotated about the axis, the guide tab of the second semi-hemispherical cup moves within the elongated track of the first semi-hemispherical cup.

9. The acetabular prosthesis of claim 8, wherein the elongated track comprises an elongated opening and wherein the guide tab of the second semi-hemispherical cup is insertable into the elongated opening when the second semi-hemispherical cup is nested into the first semi-hemispherical cup.

10. The acetabular prosthesis of claim 8, wherein the guide tab is captured within elongated track such that the inner cup cage is secured to the outer cup cage.

11. A method of performing an orthopaedic surgical procedure on a hip of a patient, the method comprising:
    inserting an outer cup cage of an acetabular prosthesis into an acetabulum of the patient, the outer cup cage including a first semi-hemispherical cup and a first mounting flange extending from a rim of the first semi-hemispherical cup;
    inserting an inner cup cage of the acetabular prosthesis into the outer cup cage, wherein the inner cup cage includes a second semi-hemispherical cup and a second mounting flange extending from a rim of the second semi-hemispherical cup and wherein inserting the inner cup cage comprises nesting the second semi-hemispherical cup into the first semi-hemispherical cup;
    rotating at least one of the inner cup cage and the outer cup cage relative to each other about an axis extending through an apex of each of the first and second semi-hemispherical cups while the second semi-hemispherical cup is nested within the first semi-hemispherical cup to position the first mounting flange and the second mounting flange in corresponding desired positions; and
    securing the first mounting flange and the second mounting flange to the hip bone of the patient.

12. The method of claim 11, further comprising securing the first and second semi-hemispherical cups to the acetabulum of the patient.

13. The method of claim 11, further comprising inserting an acetabular cup prosthesis into the second semi-hemispherical cup of the inner cup cage.

14. The method of claim 13, further comprising securing the first and second semi-hemispherical cups and the acetabular cup prosthesis to the acetabulum of the patient using bone cement.

15. The method of claim 11, wherein inserting the inner cup cage into outer cup cage comprises inserting a guide tab of the second semi-hemispherical cup of the inner cup cage into an elongated track of the first semi-hemispherical cup of the outer cup cage.

16. The method of claim 15, wherein rotating the at least one of the inner cup cage and the outer cup cage relative to each other comprises moving the guide tab within the elongated track.

17. The method of claim 11, wherein the first mounting flange comprises an ilium mounting flange and wherein the second mounting flange comprise an ischium mounting flange, and
    wherein rotating the at least one of the inner cup cage and the outer cup cage relative to each other comprises positioning the ilium mounting flange onto the ilium of the hip of the patient and positioning the ischium mounting flange onto the ischium of the hip of the patient.

18. An acetabular prosthesis for use in a hip arthroplasty surgical procedure, the acetabular prosthesis comprising:
    an outer cup cage having a first semi-hemispherical cup and an ilium mounting flange extending from a rim of the first semi-hemispherical cup, wherein the first semi-hemispherical cup includes a closed, elongated track defined through a wall of the semi-hemispherical cup; and
    an inner cup cage having a second semi-hemispherical cup and an ischium mounting flange extending from a rim of the second semi-hemispherical cup, wherein the second semi-hemispherical cup has an outer diameter smaller than an inner diameter of the first semi-hemispherical cup that allows the second semi-hemispherical cup to be received within the first hemispherical cup and wherein the second semi-hemispherical cup includes a guide tab configured to be inserted into the closed, elongated track of the first semi-hemispherical cup; and
    an acetabular cup prosthesis having an outer diameter that is smaller than an inner diameter of the second semi-hemispherical cup that allows the acetabular cup prosthesis to be received within the second semi-hemispherical cup,
    wherein, when the second semi-hemispherical cup is received within the first semi-hemispherical cup, each of the inner cup cage and the outer cup cage are rotatable relative to each other to independently position the ilium flange and the ischium flange.

19. The acetabular prosthesis of claim 18, wherein, when the inner cup cage and the outer cup cage are rotated about the axis, the guide tab of the second semi-hemispherical cup slides within the elongated track of the first semi-hemispherical cup.

* * * * *